United States Patent [19]
Elsberry

[11] Patent Number: 5,846,220
[45] Date of Patent: Dec. 8, 1998

[54] THERAPEUTIC METHOD FOR TREATMENT OF ALZHEIMER'S DISEASE

[75] Inventor: Dennis D. Elsberry, New Hope, Minn.

[73] Assignee: Medtronic, Inc., Minneapolis, Minn.

[21] Appl. No.: 641,450

[22] Filed: Apr. 30, 1996

[51] Int. Cl.⁶ .................................................. A61M 31/00
[52] U.S. Cl. ............................... 604/49; 604/93; 128/898
[58] Field of Search .................................. 604/19, 48, 49, 604/51, 93; 128/898

[56] References Cited

U.S. PATENT DOCUMENTS

| | | | |
|---|---|---|---|
| 3,894,541 | 7/1975 | El-Shafei | 604/49 |
| 3,941,119 | 3/1976 | Corrales | 604/49 |
| 4,613,324 | 9/1986 | Ghajar | 604/49 |
| 4,686,085 | 8/1987 | Osterholm | 604/49 |
| 4,998,938 | 3/1991 | Ghajar et al. | 606/130 |
| 5,169,387 | 12/1992 | Kronner | 604/51 |
| 5,180,387 | 1/1993 | Ghajar et al. | 604/266 |
| 5,192,753 | 3/1993 | McGeer et al. | |
| 5,399,346 | 3/1995 | Anderson et al. | 423/93.21 |
| 5,405,316 | 4/1995 | Magram | 604/8 |
| 5,468,221 | 11/1995 | Schoner | 604/280 |
| 5,478,807 | 12/1995 | Cronin et al. | |
| 5,542,935 | 8/1996 | Unger et al. | 604/190 |
| 5,552,415 | 9/1996 | May | 514/324 |
| 5,643,207 | 7/1997 | Rise | 604/93 |

OTHER PUBLICATIONS

Dorland's Illustrated Medical Dictionary, W.B. Saunders Company, p. 189, 1985.

Roger, J., et al., "Clinical Trial of Indomethacin in Alzheimer's Disease", *Neurology*, Aug. 1993, pp. 1609–1611.

Meade, Elizabeth A., et al., "Differential Inhibition of Prostaglandin Endoperoxide Synthase (Cyclooxygenase) Isozymes by Aspirin and Other Non–steroidal Anti–Inflammatory Drugs", *The Journal of Biological Chemistry*, Mar. 25, 1993, vol. 268 No. 9, pp. 6610–6614.

Mitchell, Jane A., "Selectivity of Nonsteroidal Antiinflammatory Drugs as Inhibitors of Constitutive and Inducible Cyclooxygenase", *Proceedings of the National Academy of Sciences*, Dec. 15, 1993, vol. 90, No. 24, pp. 11693–11697.

Malmberg, A.B., et al., "Hyperalgesia Medicated by Spinal Blutamate or Substance P Receptor Blocked by Spinal Cyclooxygenase Inhibition", *Science*, vol. 257, Aug. 28, 1992, pp. 1276–1279.

Forloni, et al., "Expression of Amyloid Precursor Protein MRNAs in Endothelial, Neuronal and Glial Cells: Modulation by Interleukin–1" *Molecular Brain Research*, 16(1992) 128–134.

Michael Murphy, "The Molecular Pathogenesis of Alzheimer's Disease: Clinical Prospects" *The Lancet*, vol. 340: Dec. 19/26, 1992.

(List continued on next page.)

*Primary Examiner*—Wynn Wood Coggins
*Assistant Examiner*—Bhisma Mehta
*Attorney, Agent, or Firm*—Curtis D. Kinghorn; Harold R. Patton

[57] ABSTRACT

A method and apparatus for treating Alzheimer's disease is disclosed. The method comprises delivering indomethacin or nonsteroidal anti-inflammatory agents having cyclooxygenase inhibitor action directly to the hippocampus or the lateral ventricle through an implanted catheter. The catheter has a flexible distal end that is implanted directly in the hippocampus or lateral ventricle as the preferred embodiment. The distal end has either a porous tip or a closed end. Where the distal end is closed, or a plurality of elution holes are present indomethacin is delivered to the hippocampus or lateral ventricle through either the porous tip or the elution holes. The catheter is part of a system for delivering indomethacin or nonsteroidal anti-inflammatory agents having cyclooxygenase inhibitor action to the hippocampus or lateral ventricle that includes a pump coupled to the catheter for delivering the indomethacin or nonsteroidal anti-inflammatory agents having cyclooxygenase inhibitor action through the catheter to the hippocampus or lateral ventricle.

13 Claims, 7 Drawing Sheets

OTHER PUBLICATIONS

Duong, Taihung, et al., "Microtubule–Associated Proteins Tau and Amyloid P Component in Alzheimer's Disease", *Brain Research,* 603(1993) 74–86.

Piet Eikelenboom, et al., "Inflammatory Mechanisms in Alzheimer's Disease", *TIPs* Dec. 1994 (vol. 15) pp. 447–450.

Rich, J.B., et al., "Nonsteroidal Anti–Inflammatory Drugs in Alzheimer's Disease", *Neurology,* Jan. 1995, 45, pp. 51–55.

Breitner, J.C.S., et al., "Inverse Association of Anti–Inflammatory Treatments and Alzheimer's Disease: Initial results of a co–twin control study".

"New Alzheimer's Therapy Suggested" Science, vol. 260, Jun. 18, 1993, pp. 1719–1720.

THERAPEUTIC METHOD FOR TREATMENT OF ALZHEIMER'S DISEASE

BACKGROUND OF THE INVENTION

1. Field of the Invention

This invention relates to a method of treating Alzheimer's disease and more specifically relates to delivering therapeutic nonsteroidal anti-inflammatory agents directly into the central nervous system or specific brain structures.

2. Description of the Related Art

Studies support an inverse relationship between anti-inflammatory medications used for treating patients with rheumatoid arthritis and an associated low prevalence of Alzheimer's disease [J. B. Rich et.al., *Neurology* 45:51–55, 1995]. Controlled studies of twin pairs having Alzheimer's disease onset greater than 3 years provide additional support that prior treatment with anti-inflammatory medications serves a protective role in Alzheimer's disease. [J. C. S. Breitner, et.,al., *Neurology* 44:227–232, 1994] Specifically, controlled double-blinded studies have found that the anti-inflammatory agent "indomethacin" administered orally has a therapeutic benefit for mild to moderately cognitively impaired Alzheimer's disease patients, and treatment with indomethacin during early stages of the disease has a retarding affect on disease progression compared to the placebo treated control group. [J. Rogers, et.al., *Neurology* 43:1609–1612, 1993] Alzheimer's patients with moderate cognitive impairment treated with indomethacin also exhibit a reduction in cognitive decline. However, patients treated with oral indomethacin developed drug related adverse effects that required their treatment to be discontinued and their removal from the study.

Studies have shown indomethacin works at the cellular areas of the brain affected by Alzheimer's disease. These cellular areas include the hippocampus, entorhinal cortex, basal forebrain, amygdala and nucleus basalis of Meynert. In the normal brain, various enzyme systems act on amyloid precursor proteins to form peptides required for physiological brain functions including cellular membrane repair.

An example of normal amyloid protein processing is the action of an endoprotease termed "alpha-secretase." Alpha-secretase cleaves the amyloid precursor protein resulting in non-amyloidogenic peptide fragments. These non-amyloidogenic peptide fragments are required for normal cellular function (S. B. Roberts et.al., *Journal of Biological Chemistry* 269:3111–3116, 1994).

Other endoproteases, termed "beta-" and "gamma-secretases", cleave the amyloid precursor protein to form amyloidogenic fragments capable of interacting with several other cellular proteins. The interaction of the amyloidogenic fragments and other cellular proteins forms enzymes that become the foci of neurotoxicity and subsequently neuritic plaques (P. Eikelenboom, et.al., *TiPS* 15:447–450, 1994). In particular, beta-secretase cleaves the amyloid precursor protein to form fragments that result in increased calcium influx into the affected neurons. This increased calcium influx affects the intracellular pH and cytokine induction of the neurons which triggers intracellular enzymatic activation including lipoxygenase and cyclooxygenase up-regulation.

These enzymes resulting from the interaction of the amyloidogenic fragments and other cellular proteins further disrupt intracellular microtubule metabolism with inhibition of protein transport blocking neurotransmission along the neurite's axon. The result of this process is senile neuritic plaque formation and neurofibrillary tangles associated with Alzheimer's disease.

Although the specific causes for increased cellular production of altered secretase activity in specific brain regions is not well understood, it is known that this dysfunctional enzymatic activity results in progressive dendritic pruning, neuronal loss and damage with marked cognitive decrements over time.

A problem with orally administered indomethacin or other nonsteroidal anti-inflammatory drugs is unpleasant side effects including severe nausea and gastric ulcers which patients develop following chronic use. Further, with chronic oral therapy the therapeutic value diminishes over time requiring dose escalation. In addition, limited transport of indomethacin or other nonsteroidal anti-inflammatory drugs across the blood brain barrier increases the potential for systemic adverse side-effects.

In order to maintain the same therapeutic affect with disease progression, the dose of indomethacin taken orally must increase. In patients having adverse side-effects, treatment escalation is not possible. Thus, oral administration of drugs such as indomethacin is inherently dose-limiting.

In addition to the problems just mentioned with orally administered indomethacin or similar nonsteroidal anti-inflammatory drugs, the amount of drug entering the patient's blood system is minimized by uptake of the drugs by the gastrointestinal system.

It is therefore desirable to produce a chronic treatment regimen allowing the direct delivery of indomethacin or similar nonsteroidal anti-inflammatory drugs, having therapeutic value against the affect of amyloidogenic protein neurotoxicity, to the desired area of the brain. Such a treatment regimen is necessary to by-pass the adverse side-effects produced by orally administered drug and subsequent drug receptor uptake by the gastrointestinal system.

SUMMARY OF THE INVENTION

A method of treatment for Alzheimer's disease is disclosed. The method comprises delivering indomethacin or similar nonsteroidal anti-inflammatory drugs through an implanted catheter positioned directly into the hippocampus with a delivery catheter attached to a drug delivery pump containing the therapeutic drug. The catheter has a flexible distal end that is implanted directly in the hippocampus. Alternatively, the distal end of the catheter may be positioned within the lateral ventricles of the cerebroventricular system which communicates anatomically via the inferior horn of the lateral ventricle immediately adjacent to the hippocampus.

The distal end has either a porous tip or a closed end. Where the distal end is closed, a plurality of elution holes are present. Indomethacin or a similar drug is delivered to the hippocampus directly or indirectly via the cerebroventricular system. A pump is coupled to the catheter for delivery of the drug at a selected infusion rate. The combination of a catheter implanted directly in the brain and a pump to pump the drug through the catheter and out the distal end of the catheter into the brain allows direct access across the blood brain barrier. Thus, less drug is required for the desired therapeutic affect compared to oral or systemic delivery since drug is targeted within the central nervous system. Further, drug delivery directly to the brain limits drug access into the systemic circulation preventing access to secondary therapeutic targets associated with adverse side-effects associated with oral or systemic drug delivery.

The catheter preferably comprises a first tubular portion that has a generally cylindrical lumen of a first internal diameter and is composed of a relatively impermeable flexible material. A second tubular portion has an open end disposed within the lumen and a closed distal end disposed without the lumen. The second tubular portion is composed of a flexible, porous material having a preselected microporosity that is operable to permit the therapeutic drug, for example indomethacin, to flow from the catheter into the hippocampus. The second tubular portion is selectively moveable with respect to the first tubular portion.

Alternatively, a catheter for delivering indomethacin or a similar drug to a selected site within the hippocampus comprises a tubular portion composed of a relatively impermeable material. The distal end of the tubular portion is closed and has one or more elution holes through which indomethacin contained within the tubular portion exits the catheter.

It is therefore an object of the invention to provide a method and device for treating Alzheimer's disease.

It is another object of the invention to administer indomethacin or another similar drug more effectively to the brain.

It is another object of the invention to administer indomethacin or another similar drug directly to the area of interest in the brain.

It is another object of the invention to administer indomethacin or another similar drug in tightly controlled amounts to the brain.

It is another object of the invention to administer indomethacin or another similar drug in minute dosages over time to the brain.

It is another object of the invention to continuously administer indomethacin or another similar drug over time to the brain.

It is another object of the invention to administer indomethacin or another similar drug over time to the hippocampus in the brain.

It is another object of the invention to administer indomethacin or another similar drug over time to the lateral ventricles in the brain.

It is another object of the invention to administer indomethacin or another similar drug over time to the marginal aspects of the lateral ventricles in the brain.

It is another object of the invention to administer indomethacin or another similar drug to the brain directly across the blood brain barrier.

These objects and advantages of the invention, as well as others that will be clear to those skilled in the art, will become apparent upon reading the following detailed description and references to the drawings. In the drawings and throughout this disclosure, like elements wherever referred to, are referenced with like reference numbers.

DESCRIPTION OF THE PREFERRED EMBODIMENTS

In the invention, indomethacin or a similar drug is delivered directly into a patient's hippocampus 18. Throughout this disclosure, reference to indomethacin includes reference to drugs similar to indomethacin. Some of these drugs include therapeutic nonsteroidal anti-inflammatory agents such as lipoxygenase or cyclooxygenase inhibitors. Such nonsteroidal anti-inflammatory agents having cyclooxygenase inhibitor action may include: acetaminophen, ibuprofen, fenoprofen, flurbiprofen, ketoprofen, naproxen, piroxicam, zomepirac, diclofenace, and sulindac, whereas nordihydroguaiaretic acid is a potent inhibitor of 5-lipoxygenase. Also throughout this disclosure, unless stated otherwise, reference to a patient's hippocampus 18 also refers to a patient's lateral ventricle which lies immediately adjacent to the hippocampus 18.

Figure 1:
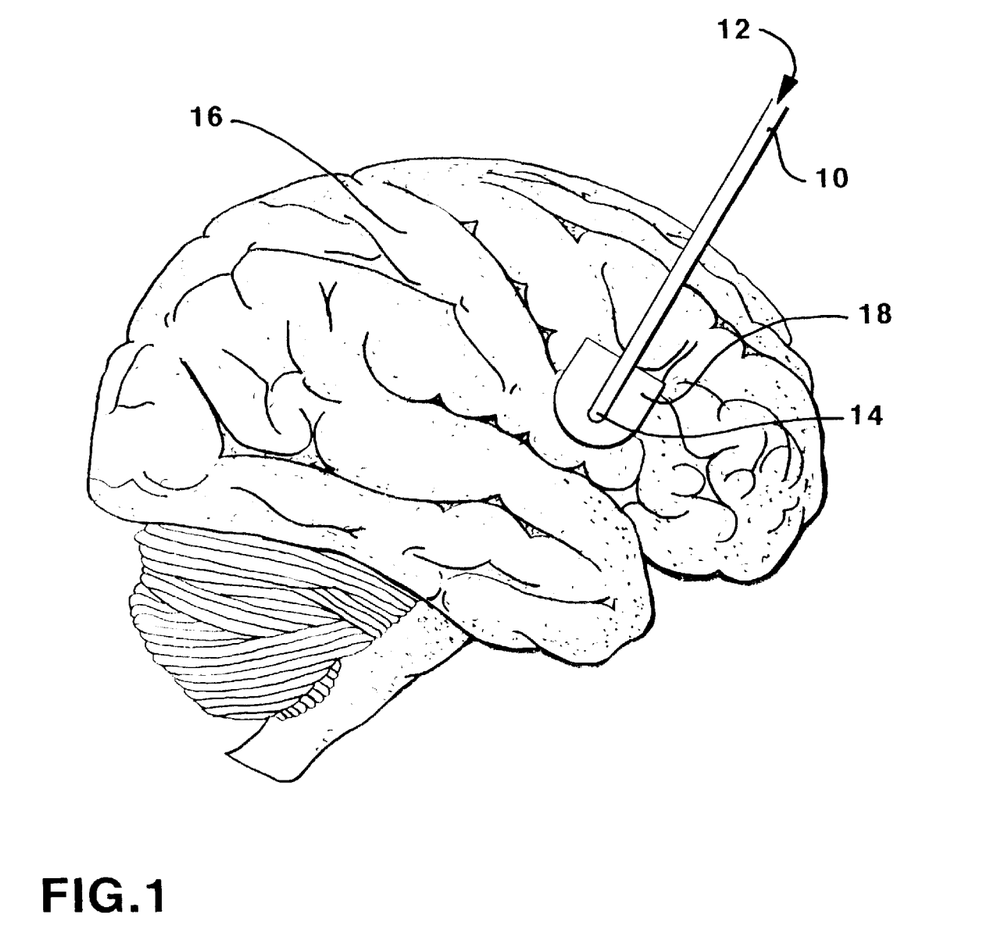
FIG. 1 is a sagittal view of a human brain with a catheter placed so that the distal end of the catheter is positioned in the hippocampus.
Figure 2A:
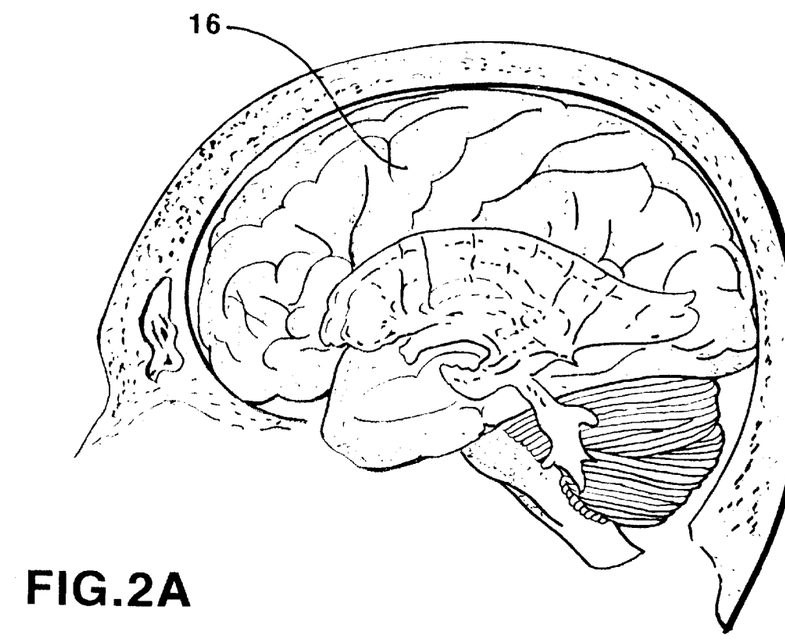
FIG. 2A is a sagittal view of the human brain with the relationship of the hippocampus with respect to the lateral ventricle.
Figure 2B:
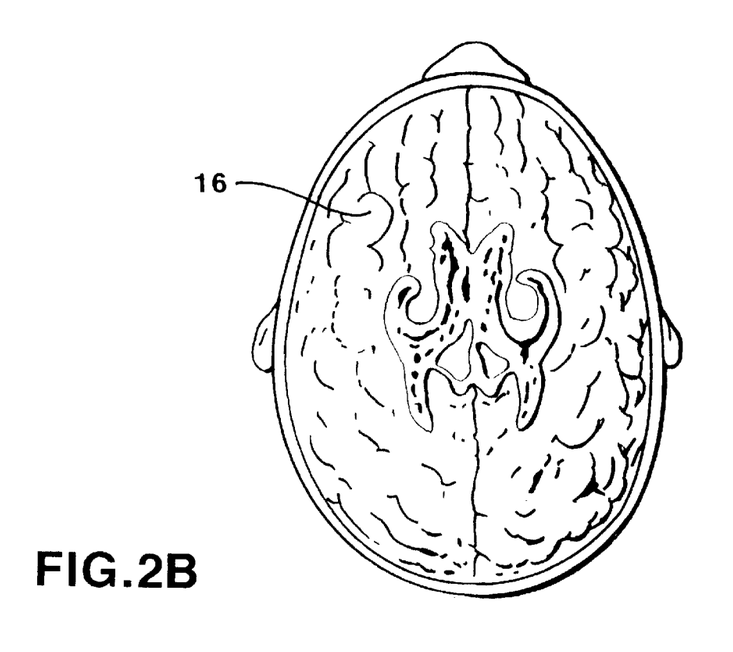
FIG. 2B is a superior view of the relationship of the hippocampus with respect to the inferior horn of the lateral ventricle.

As shown in FIG. 1, this is accomplished by implanting a catheter 10 having a proximal end 12 and a distal end 14 in a patient's brain 16 so that distal end 14 is located in the patient's hippocampus 18. FIGS. 2A and 2B are transverse and coronal views of the human brain 16 illustrating the relationship of the hippocampus 18 to the lateral ventricle 11.

Figure 3:
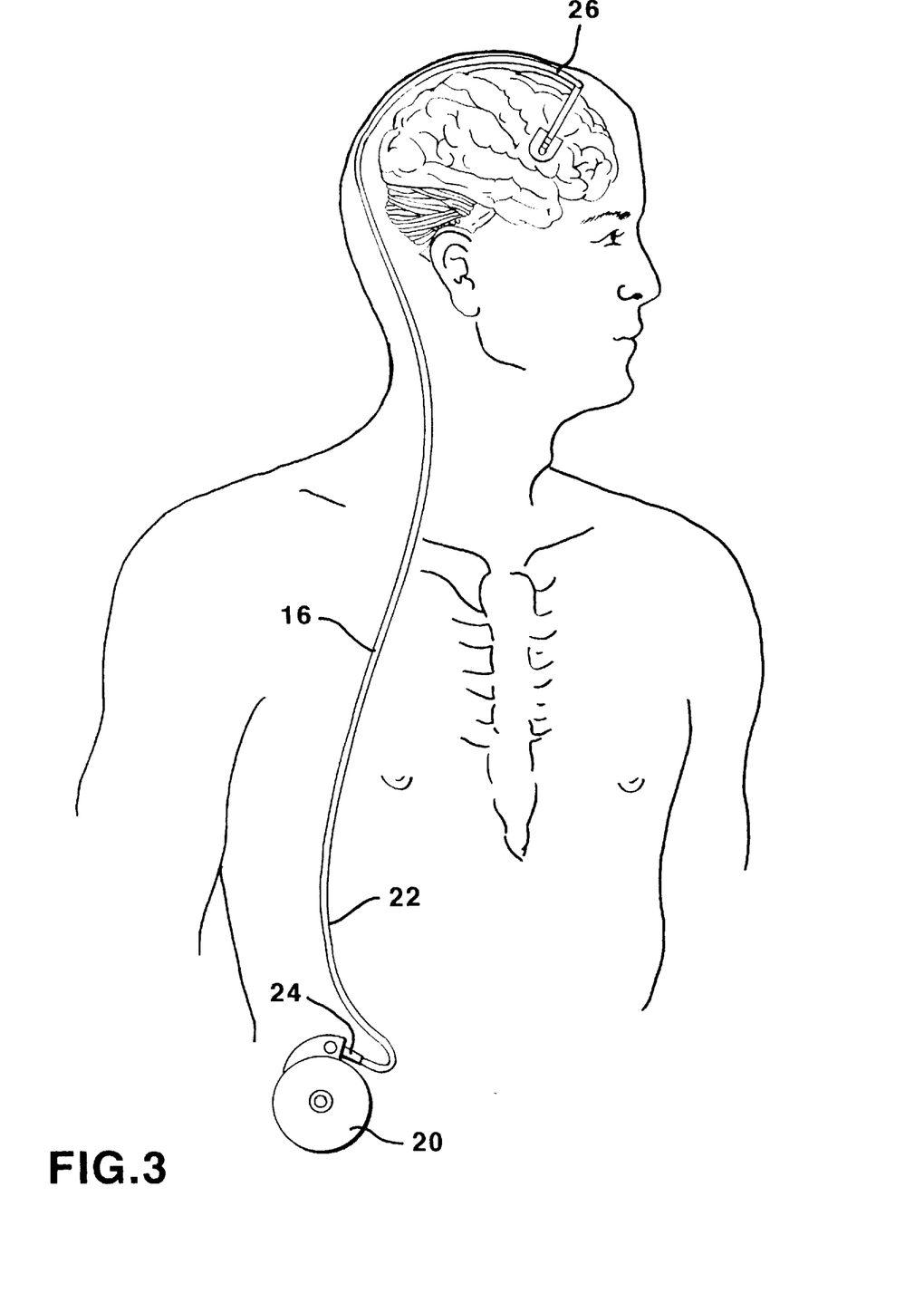
FIG. 3 is a schematic depiction of the preferred embodiment of a means for implementing the invention with direct access into the hippocampus.

In the invention, proximal end 12 is attached to a source of indomethacin. This is preferably accomplished by attaching proximal end 12 to an implantable infusion pump ("IIP") 20 through a connecting catheter 22 having a proximal end 24 and distal end 26. Distal end 26 is attached to IIP 20 as shown in FIG. 3. Alternately, proximal end 12 may be attached to a source of indomethacin by being connected via an implanted access port ("CAP") 27 for percutaneous access to an external infusion pump 28 as shown in FIG. 3A. The combination of IIP 20 with catheter 10 is preferred because, as will be explained hereafter, it is believed to be more safe for continuously infusing indomethacin to the hippocampus 18 to obtain the maximum therapeutic effect. Use of IIP 20 allows indomethacin to be administered in tightly controlled, yet minute dosages over time.

Figure 4:
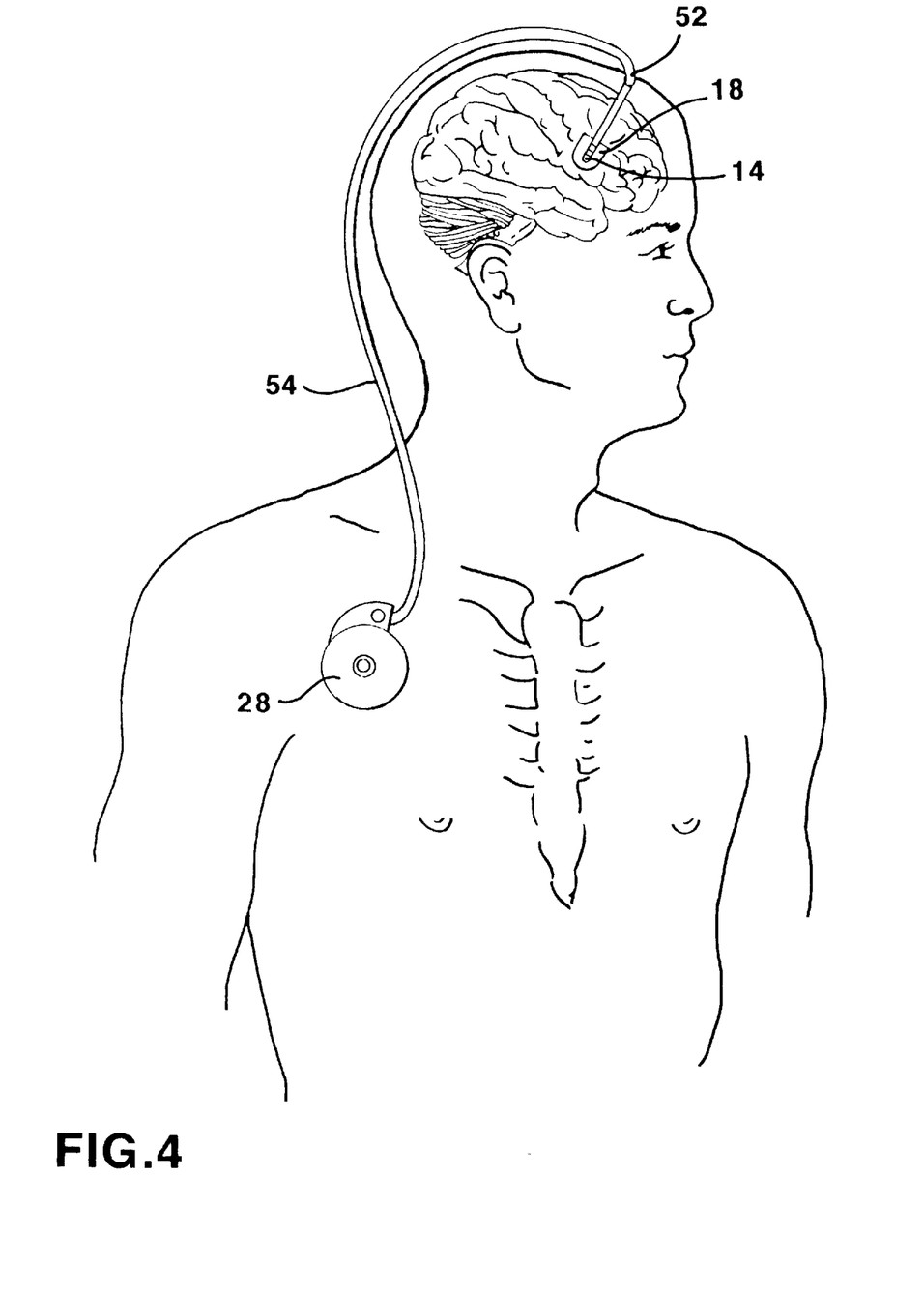
FIG. 4 is a schematic depiction of an alternate embodiment of a means for implementing the invention with direct access into the lateral ventricle.

In the invention alternately, indomethacin is delivered directly to a patient's lateral ventricle 11. As shown in FIG. 4, this is accomplished by implanting a catheter 10 having a proximal end 12 and a distal end 14 in a patient's brain so that the distal end 14 is located in the patient's lateral ventricle 11.

In the invention, proximal end 12 is attached to a source of indomethacin. This is preferably accomplished by attaching proximal end 12 to an IIP 20 through a connecting catheter 22 having a proximal end 24 and a distal end 26. Distal end 26 is attached to proximal end 12 while proximal end 24 is attached to IIP 20. Alternately, proximal end 12 may by attached to a source of indomethacin by being connected to an external infusion pump 28 as shown in FIG. 4A. The combination of IIP 20 with catheter 10 is preferred to continuously infuse indomethacin to the lateral ventricle 11. The alternate infusion of indomethacin to the lateral ventricle 11 allows for safe access for perfusing the marginal aspect of hippocampus 18.

Figure 5:
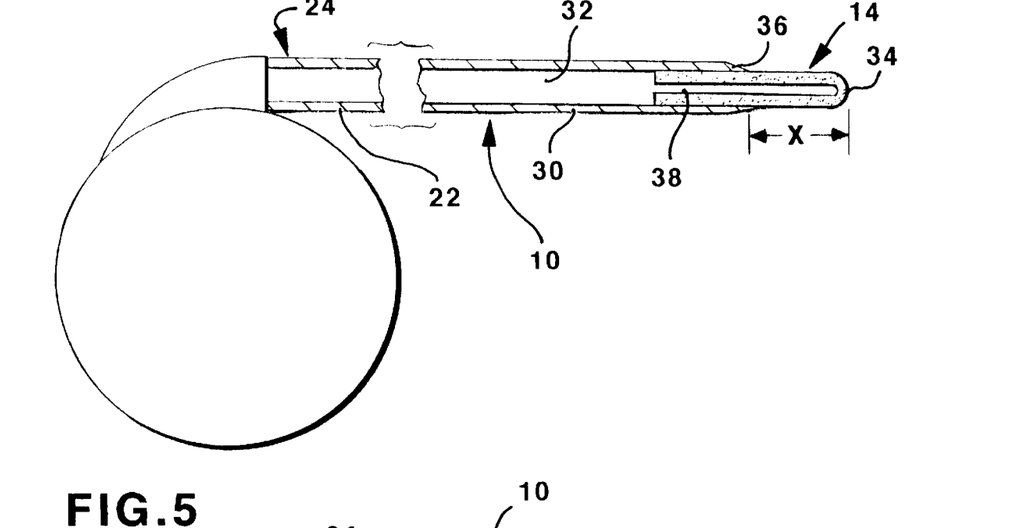
FIG. 5 is a schematic side view depiction of a preferred embodiment of a catheter attached to an infusion pump used in implementing the method of the invention.

The detailed structure of a preferred embodiment of catheter 10 is shown in FIG. 5. Catheter 10 and distal end 14 are shown in an enlarged cross sectional view. The size of catheter 10 is not shown for simplicity of illustration.

As has been mentioned, proximal end 12 is preferable coupled to distal end 26 of connecting catheter 22 and the proximal end 24 of connecting catheter 22 is attached to IIP 20. The connection between proximal end 12 and distal end 26 and the connection between proximal end 24 and IIP 20 is shown schematically in FIG. 5. It should be understood that the actual types of connection will vary depending upon the particular type of connecting catheter 22 and IIP 20 or CAP used as will be well understood by those skilled in the art.

Catheter 10 preferably comprises an elongated tubular portion 30 having a central lumen 32. Catheter 10 terminates at the most distal end of distal end 14 in tip 34. Tubular portion 30 preferably composed of a material that will expand in response to an external stimulus such as heat or a chemical solvent.

In one preferred embodiment, the tubular portion 30 is composed of a relatively impermeable material such as polyacrylonitrile. Polyacrylonitrile will expand in response to an external stimuli such as heat, and will return to its original shape upon cooling.

In an alternate preferred embodiment, tubular portion 30 is composed of enhanced tear resistant silicone elastomer or polyurethane, which, when exposed to an external stimulus such as a chemical solvent like freon, will expand. When the solvent evaporates, the silicone elastomer or polyurethane will return to its original shape.

Whether a heat sensitive or solvent sensitive material is used, the tubular portion 30 should be biocompatible and sufficiently flexible to facilitate insertion. A durometer shore value of 80A is preferred. Tip 34 is preferably rounded to minimize tissue disruption during insertion and location of distal end 14 as will be described hereafter. Tubular portion 30 preferably has an externally tapered distal end surface 36 to minimize tissue disruption during insertion.

Catheter tip 34 has a generally tubular shape and is designed to fit snugly within lumen 32. Catheter tip 34 has a lumen 38 to receive indomethacin from lumen 32. Lumen 32 and the external diameter of catheter tip 34 should be sized so that there is a zero tolerance therebetween. A snug fit is desirable to maintain the position of catheter tip 34 in relation to tubular portion 30 and to discourage seepage of indomethacin between the interface of the exterior of catheter tip 34 and the interior surface of tubular portion 30. However, as discussed more fully below, under certain conditions, catheter 10 may be customized by moving catheter tip 34 in relation to tubular portion 30.

Catheter tip 34 is preferable composed of a porous material such as polysulfone hollow fiber, manufactured by Amicon, although polyethylene, polyamides, polypropylene and expanded polytetrafluoroethylene (ePTFE) are also suitable. Catheter tip 34 is preferable porous along its entire length to enable indomethacin to flow into the hippocampus 18. The preferred pore size is approximately ranged between 0.1–0.2 microns.

It is preferred that the maximum pore size be less than or equal to approximately 0.2 microns to prevent any bacterial agent that may be present inside catheter 10 from entering into the hippocampus 18 or lateral ventricle 11. Furthermore, at larger pore sizes, there is the potential for tissue in-growth that may restrict the flow of indomethacin out of catheter tip 34. By making the entire length of catheter tip 34 porous, a more uniform volume distribution of indomethacin is provided. Unlike a catheter tip that has a single elution hole or a few elution holes, catheter tip 34 in this embodiment dispenses indomethacin in a nearly 360 degree pattern along the entire length of catheter tip 34 that is exposed to the hippocampus 18 or lateral ventricle 11.

Although the preferred embodiment of catheter tip 34 is a porous tip along its entire length, it is also possible to have a catheter tip 34 that has a single elution hole or a few elution holes along its length. Throughout this disclosure, the length of the portion of catheter tip 34 that is exposed to the hippocampus 18 or lateral ventricle 11, whether catheter tip 34 is continuously porous or has one or a few elution holes, is represented by "x."

As described above, tubular portion 30 is composed of a material that will expand in response to an external stimulus such as hear or a chemical solvent. As a result, length x may be custom selected by the physician at the time of insertion. When tubular portion 30 expands in response to the external stimulus, the snug fit between catheter tip 34 and tubular portion 30 is relieved, and the physician may slide catheter tip 34 with respect to tubular portion 30 by hand to achieve the desired length x. The material from which tubular portion 30 is composed, is selected so that when the external stimulus is removed, tubular portion 30 returns to its ordinary shape, thereby reestablishing the near zero tolerance fit between tubular portion 30 and catheter tip 34.

Alternately, length x may be set at the time of manufacture. Catheters 10 may be manufactured having a variety of lengths x for the portion of catheter tip 34 that will be exposed to the hippocampus 18 or lateral ventricle 11. Lengths x are preselected to produce catheters 10 for predetermined applications in the hippocampus 18 or lateral ventricle 11. These applications may be determined by the specific location in the hippocampus 18 where distal end 14 will be located and the size of the hippocampus 18 of a particular patient. Once the length x has been determined for a catheter 10, the length x may be established on catheter tip 34 and catheter tip 34 may be attached to tubular portion 30 as described above.

Figure 6:
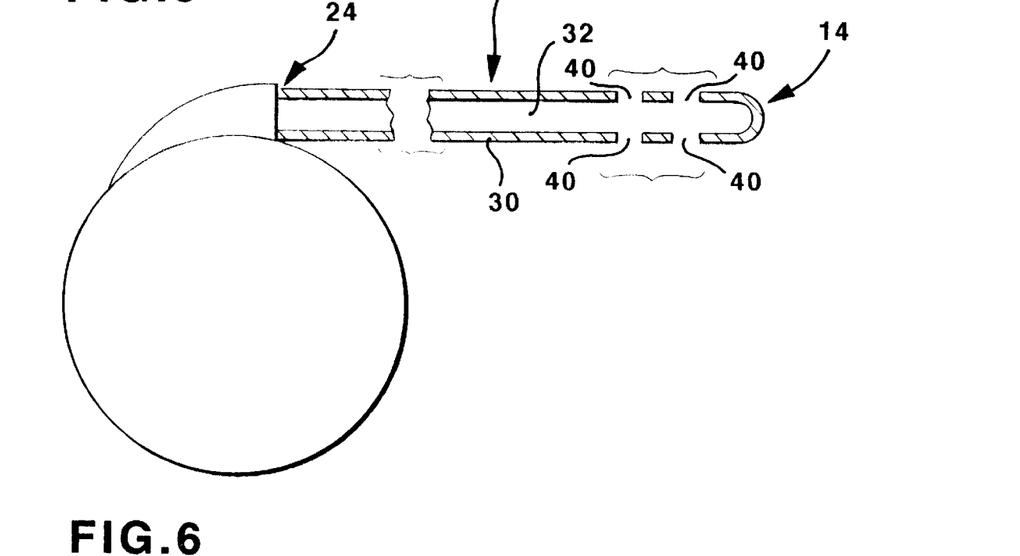
FIG. 6 is a schematic side view depiction of an alternate embodiment of catheter attached to an infusion pump used in implementing the method of the invention.

In an alternate design for catheter 10, chosen in FIG. 6, distal end 14 is closed. One or a plurality of elution holes 40 extent through distal end 14 so that the indomethacin flowing through catheter 10 may exit catheter 10 through elution holes 40. In this embodiment, the entire catheter 10 is preferably made of a relatively impermeable material such as polyacrylonitrile, polyethylene, polypropylene, or silicone elastomer.

In any of the embodiments for catheter 10, distal end 14 must be sufficiently pliable so that it may move to conform to the structure of the brain in the hippocampus 18 or lateral ventricle 11 as catheter 10 is implanted in the patient as will be described hereafter. This compliance may be accomplished by polymer compositions of low durometer materials.

To practice the invention, distal end 14 is surgically implanted in the brain 16 with distal end 14 specifically located in the patient's hippocampus 18 or lateral ventricle 11. This is preferably done by accessing the hippocampus 18 through a posterior occipital lobe. This produces the least damage to the patient's motor cortex. Similarly, accessing the lateral ventricle 11 may be performed anteriorially through the frontal lobe or posteriorially through the occipital lobe to prevent damaging the motor cortex and affecting the patient's motor function. Typically a trocar 42 or catheter 10 containing a stylet 44 is introduced through the selected lobe to the patient's hippocampus 18 or lateral ventricle 11. Access and location of the trocar 42 or catheter 10 containing a stylet 44 is preferably done using well known external triangulation techniques, stereotactic placement techniques, or magnetic resonance imaging (MRI) techniques such as are commonly used, among other things, in the placement of hydrocephalic shunts.

Figure 8:
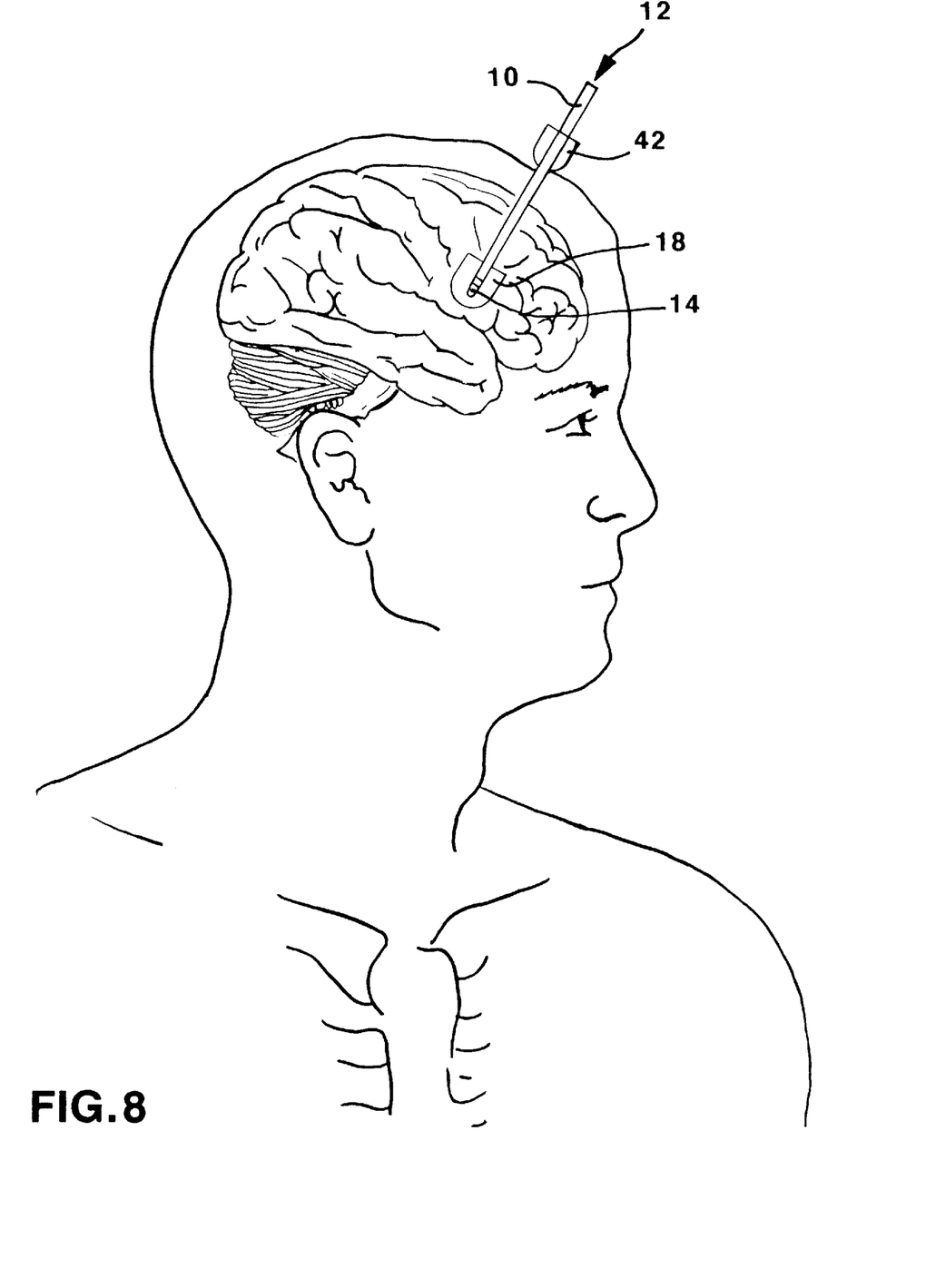
FIG. 8 is a schematic side view depiction of a catheter placed in the hippocampus according to the teachings of the invention.

As shown in FIG. 8, where a trocar 42 is used to access the hippocampus 18, once the trocar 42 is located in the hippocampus 18, catheter 10 is passed through the trocar 42 so that distal end 14 leaves the trocar 42 and enters the hippocampus 18. Once distal end 14 is free of the trocar 42, because distal end 14 is pliable, distal end 14 will move to accommodate the structure of the hippocampus 18. After distal end 14 is located in the hippocampus 18, the trocar 42 is removed. Proximal end 12 is attached to a source of indomethacin.

Figure 9:
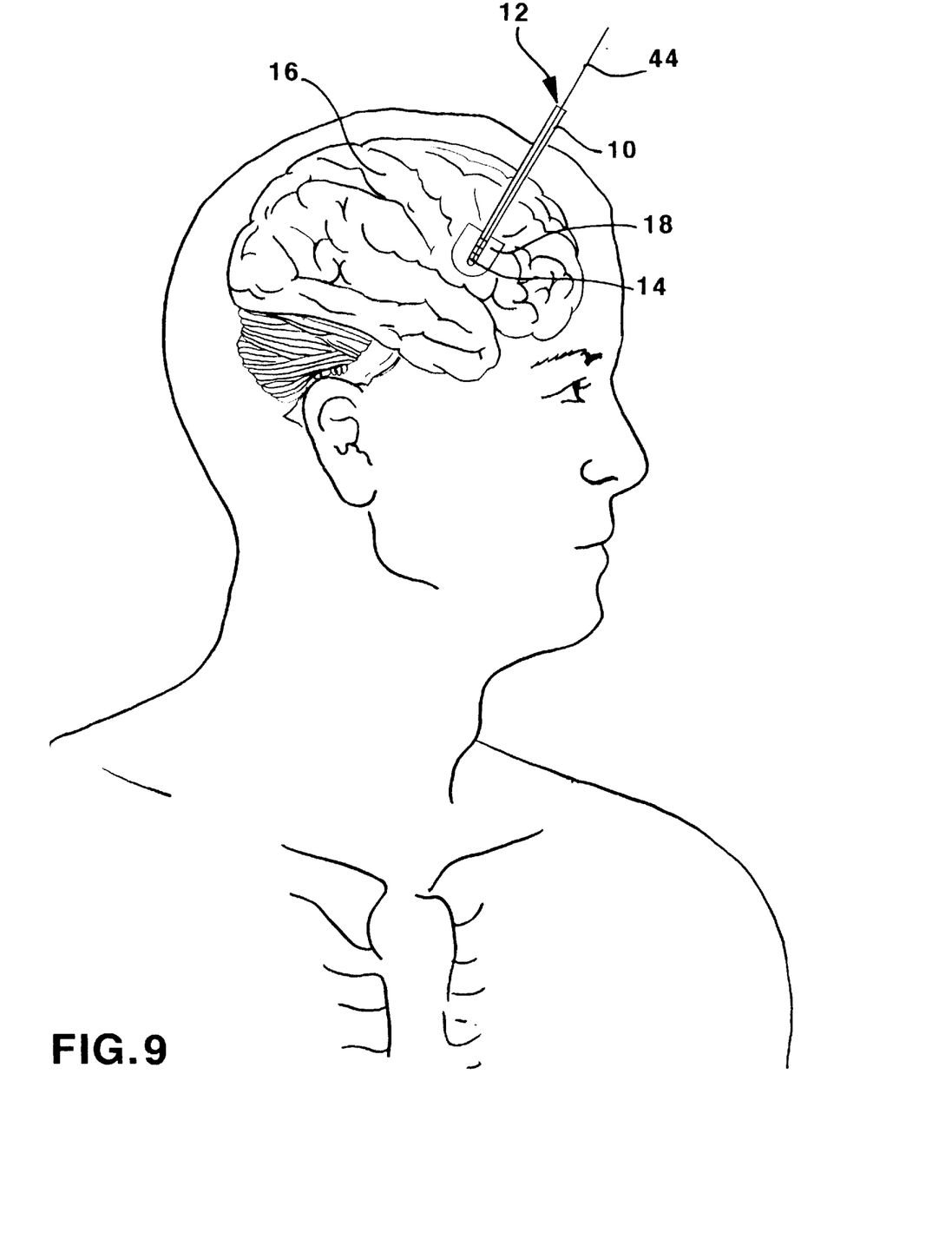
FIG. 9 is a schematic side view depiction of a catheter placed in the lateral ventricle according to the teachings of the invention.

As shown in FIG. 9 where catheter 10 is located in the hippocampus 18 using a stylet 44, a stylet 44 is placed in lumen 32 to add rigidity to catheter 10. Distal end 14 is then moved to the desired location in the hippocampus 18 or lateral ventricle 11. When distal end 14 is determined to be at the desired location in the hippocampus 18 or lateral ventricle 11, the stylet is removed. When the stylet 44 is removed, because distal end 14 is pliable, distal end 14 will adapt itself to the internal structure of either the hippocampus 18 or lateral ventricle 11. After the stylet 44 is removed, proximal end 12 is attached to a source of indomethacin.

Figure 7:
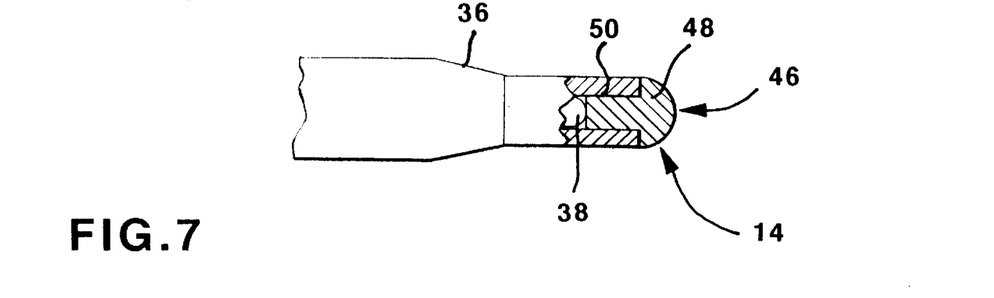
FIG. 7 is a schematic side view depiction of a marker tip used with the catheters of FIGS. 5 and 6.

It is preferred to place some means for locating distal end 14 during the access and location process. This is preferably done by applying a marker 46, as shown in FIG. 7, to distal end 14, that is detected during the access and location process. If access and location is accomplished using some form of x-ray radiation, marker 46 is preferably radiopaque. Radiopaque marker 46 renders at least a portion of distal tip 14 opaque to x-rays, enabling the tip 34 to be observed via fluoroscopy or via x-ray during access and location of catheter 10.

In a preferred embodiment, the marker 46 comprises a semispherical portion 48 that has a cylindrical nipple 50 emanating away therefrom. Hemispherical portion 48 provides a rounded profile for minimizing tissue disruption during insertion. Cylindrical nipple 50 is sized to fit snugly within the lumen 38 and is held in place via a suitable biocompatible adhesive, such as a biocompatible medical silicone adhesive or a medical urethane adhesive..

In a preferred embodiment, radiopaque marker 46 comprises tantalum powder dispersed in a matrix composed of a biocompatible adhesive, such as those discussed above. The preferred ratio of tantalum to adhesive is 3 to 2. Ordinarily, radiopaque marker 46 will be premolded prior to insertion into the lumen 38. After radiopaque marker 46 has been inserted into the lumen 38, a thin coating of the same biocompatible adhesive is preferably applied to the exterior of the hemispherical portion 48. Other materials may also be suitable for radiopaque marker 46, such as barium or platinum materials.

Alternately, the radiographic marker 46 may be chosen of a material that has sufficient radiodensity for visualization during radiologic procedures, but in powdered form that is dispersed in the catheter tip 34 at the time the catheter tip 34 is molded.

Alternatively, marker 46 may be composed of a material that is compatible to nuclear magnetic resonance imaging (MRI) to enable the tip 34 to be detected during a MRI scan. Preferred material for such a marker 46 is platinum, though barium, tantalum, and similar materials are also suitable. Regardless of whether radiography or MRI is being utilized, the goal of providing a radiographic marker 46 is to enable the operator to accurately detect the precise location of the tip 34 to facilitate placement and later verification of the integrity and position of distal end 14 of catheter 10.

After distal end 14 has been located in the hippocampus 18, proximal end 12 of catheter 10 is attached to a source of indomethacin. Where the source of indomethacin is IIP 20, proximal end 12 is attached to distal end 26 of connecting catheter 22. Connecting catheter 22 is subsequently tunneled subcutaneously under the scalp, behind the ear and to a pectoral or abdominal site where IIP 20 will be implanted. IIP 20 may be any of a number of commercially available implantable infusion pumps such as, for example, the SynchroMed® pump, Model 8611H, manufactured by Medtronic, Inc., Minneapolis, Minn.

Alternately, after distal end 14 has been located in the hippocampus 18 or lateral ventricle 11, proximal end 12 of catheter 10 may be attached to an external source of indomethacin. In this case, proximal end 12 is attached to an access port 52 placed in the patient's skull. Access port 52 is in turn connected to a connecting catheter 54 that is attached to an external pump 28 that is connected to a reservoir of indomethacin (not shown). Pump 28 may be any of a number of commercially available external infusion pumps such as, for example, Pharmacia Deltec, Inc. ambulatory infusion pumps.

Once distal end 14 has been located in the hippocampus 18 or lateral ventricle 11 and proximal end 12 has been attached to either IIP 20 or an external pump 28, indomethacin is infused through catheter 10 to exit catheter 10 distal end 14. In the embodiment of catheter 10 having a porous distal end 24, indomethacin exits catheter 10 through the porous material. In the embodiment of catheter 10 having a closed distal end 14, indomethacin exits catheter 10 through elution holes 40. In either embodiment for distal end 14, the following are believed to be desirable dosages and flow rates for the introduction of indomethacin into the hippocampus 18 ranging from 0.1–1.0 microliters per hour.

It is believed that the disclosed invention will have particular therapeutic value if indomethacin is continually infused to the patient's hippocampus 18. Therefore, in selecting the material for catheter 10, care should be taken to ensure that the materials chosen is compatible with long term exposure to indomethacin.

By practicing the disclosed invention, the unpleasant side effects associated with orally administering indomethacin or similar drugs are eliminated. In addition, higher concentrations of indomethacin may be presented to the hippocampus 18 or the lateral ventricles of the cerebroventricular system than is possible with orally administered indomethacin.

Many modifications and variations may be made in the techniques and structures described and illustrated herein without departing from the spirit and scope of the present invention. For example, the system could be used to infuse a cytostatic agent into a malignant mass located in the variety of places in the body or infuse a nerve growth factor into the intrathecal space of the spinal column. Accordingly, the techniques and structures described and illustrated here in should be understood to be illustrative only and not limiting upon the scope of the present invention.

What is claimed is:

1. A method of treating Alzheimer's disease comprising the steps of:

implanting the distal end of a catheter having a distal end and a proximal end in a patient's hippocampus;

attaching the proximal end of the catheter to a source of indomethacin;

infusing indomethacin through the catheter to exit the distal end of the catheter in the patient's hippocampus.

2. The method of claim 1 wherein the step of implanting includes the steps of:

introducing a trocar into the patient's hippocampus;

passing the catheter through the trocar so that the distal end of the catheter leaves the trocar and enters the hippocampus;

removing the trocar leaving the catheter in place.

3. The method of claim 1 wherein the step of implanting includes the step of:

introducing a catheter containing a stylet through a selected lobe to the patient's hippocampus;

removing the stylet leaving the catheter in place.

4. A method of treating Alzheimer's disease comprising the steps of:

implanting the distal end of a catheter having a distal end and a proximal end in a patient's lateral ventricle;

attaching the proximal end of the catheter to a source of indomethacin;

infusing indomethacin through the catheter to exit the distal end of the catheter in the patient's lateral ventricle.

5. The method of claim 4 wherein the step of implanting the distal end of a catheter includes the step of anteriorally accessing the lateral ventricle through the frontal lobe.

6. The method of claim 4 wherein the step of implanting includes the steps of:

introducing a trocar into the patient's lateral ventricle;

passing the catheter through the trocar so that the distal end of the catheter leaves the trocar and enters the lateral ventricle;

removing the trocar leaving the catheter in place.

7. The method of claim 4 wherein the step of implanting includes the step of:

introducing a catheter containing a stylet through a selected lobe to the patient's lateral ventricle;

removing the stylet leaving the catheter in place.

8. A method of treating Alzheimer's disease comprising the steps of:

implanting the distal end of a catheter having a distal end and a proximal end in a patient's hippocampus or lateral ventricle, wherein the patient's hippocampus or lateral ventricle is accessed through a posterior occipital lobe;

attaching the proximal end of the catheter to a source of indomethacin;

infusing indomethacin through the catheter to exit the distal end of the catheter in the patient's hippocampus or lateral ventricle.

9. A method of treating Alzheimer's disease comprising the steps of:

implanting the distal end of a catheter having a distal end and a proximal end in a patient's hippocampus or lateral ventricle, wherein the patient's hippocampus or lateral ventricle is accessed posteriorally through the occipital lobe;

attaching the proximal end of the catheter to a source of indomethacin;

infusing indomethacin through the catheter to exit the distal end of the catheter in the patient's hippocampus or lateral ventricle.

10. A method of treating Alzheimer's disease comprising the steps of:

implanting, through a posterior occipital lobe, the distal end of a catheter having a distal end and a proximal end in a patient's hippocampus;

attaching the proximal end of the catheter to a source of indomethacin;

infusing indomethacin through the catheter to exit the distal end of the catheter in the patient's hippocampus.

11. A method of treating Alzheimer's disease comprising the steps of:

implanting, posteriorally through the occipital lobe, the distal end of a catheter having a distal end and a proximal end in a patient's lateral ventricle;

attaching the proximal end of the catheter to a source of indomethacin;

infusing indomethacin through the catheter to exit the distal end of the catheter in the patient's lateral ventricle.

12. A method of treating Alzheimer's disease comprising the steps of:

implanting the distal end of a catheter having a distal end and a proximal end in a patient's hippocampus;

attaching the proximal end of the catheter to a source of nonsteroidal anti-inflammatory agents having cyclooxygenase inhibitor action;

infusing nonsteroidal anti-inflammatory agents having cyclooxygenase inhibitor action through the catheter to exit the distal end of the catheter in the patient's hippocampus.

13. A method of treating Alzheimer's disease comprising the steps of:

implanting the distal end of a catheter having a distal end and a proximal end in a patient's lateral ventricle;

attaching the proximal end of the catheter to a source of nonsteroidal anti-inflammatory agents having cyclooxygenase inhibitor action;

infusing nonsteroidal anti-inflammatory agents having cyclooxygenase inhibitor action through the catheter to exit the distal end of the catheter in the patient's lateral ventricle.

* * * * *